United States Patent [19]

Schenk et al.

[11] 4,145,353
[45] Mar. 20, 1979

[54] PROCESS FOR REMOVING 1,4-NAPHTHOQUINONE FROM PHTHALIC ANHYDRIDE

[75] Inventors: Norbert Schenk, Leverkusen; Paul Losacker, Leichlingen; Manfred Martin, Cologne, all of Fed. Rep. of Germany

[73] Assignee: Bayer Aktiengesellschaft, Leverkusen, Fed. Rep. of Germany

[21] Appl. No.: 850,516

[22] Filed: Nov. 10, 1977

[30] Foreign Application Priority Data

Dec. 1, 1976 [DE] Fed. Rep. of Germany ....... 2654405

[51] Int. Cl.² ........................................... C07D 307/89
[52] U.S. Cl. ................................. 260/346.7; 260/369; 260/346.4
[58] Field of Search .................... 260/346.4, 346.7, 369

[56] References Cited

U.S. PATENT DOCUMENTS

| 3,870,730 | 3/1975 | Scharfe et al. ....................... 260/369 |
| 4,026,770 | 5/1977 | Scharfe et al. ................. 260/346.7 X |

Primary Examiner—Richard L. Raymond
Attorney, Agent, or Firm—Sprung, Felfe, Horn, Lynch & Kramer

[57] ABSTRACT

A process for removing 1,4-naphthoquinone from phthalic anhydride has now been found, which is characterized in that phthalic anhydride containing 1,4-naphthoquinone, or mixtures containing phthalic anhydride and also containing 1,4-naphthoquinone, are subjected to a heat treatment at temperatures from 200° to 300° C. in the presence of 1,4,4a,9a-tetrahydroanthraquinone.

14 Claims, 1 Drawing Figure

U.S. Patent        Mar. 20, 1979        4,145,353
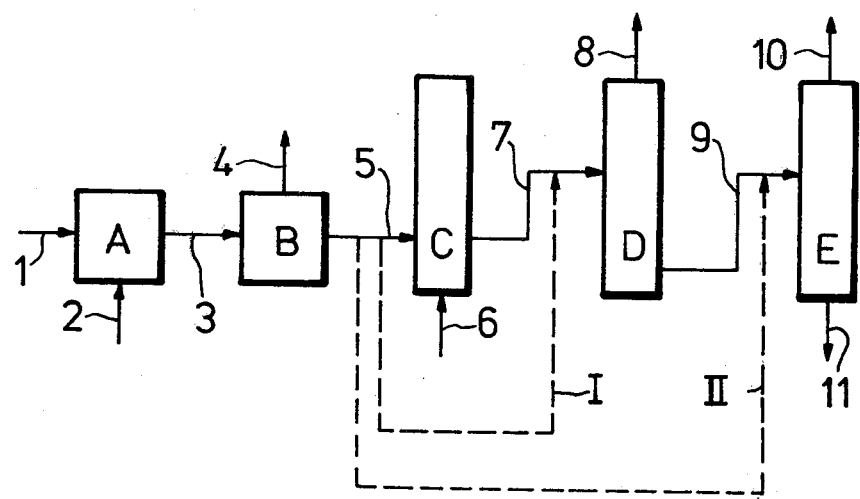

PROCESS FOR REMOVING 1,4-NAPHTHOQUINONE FROM PHTHALIC ANHYDRIDE

The present invention relates to a process for removing 1,4-naphthoquinone from phthalic anhydride by treating the phthalic anhydride-containing 1,4-naphthoquinone with 1,4,4a,9a-tetrahydroanthraquinone or mixtures containing 1,4,4a,9a-tetrahydroanthraquinone.

It is known from Ullmann, Encyclopädie der technischen Chemie (Encyclopaedia of Industrial Chemistry), 3rd edition, volume 13, pages 720-721 that phthalic anhydride which has been obtained by gas phase oxidation of naphthalene can contain small amounts of 1,4-naphthoquinone. It is further known from this publication that 1,4-naphthoquinone can be removed from phthalic anhydride by subjecting the crude phthalic anhydride to a heat treatment with concentrated sulphuric acid. After the heat treatment, the excess sulphuric acid is neutralised by added chalk. Distillation then gives a phthalic anhydride which has been freed from 1,4-naphthoquinone. Disadvantages in this process are the corrosion resulting from the presence of sulphuric acid and the formation of solid residues during distillation, occasioned by the addition of chalk. This process can, therefore, virtually only be carried out discontinuously.

The present invention is based on the object of avoiding these disadvantages and providing a process for removing 1,4-naphthoquinone from phthalic anhydride which can be carried out continuously.

A process for removing 1,4-naphthoquinone from phthalic anhydride has now been found, which is characterised in that phthalic anhydride containing 1,4-naphthoquinone, or mixtures containing phthalic anhydride and also containing 1,4-naphthoquinone, are subjected to a heat treatment at temperatures from 200° to 300° C. in the presence of 1,4,4a,9a-tetrahydroanthraquinone.

1,4,4a,9a-Tetrahydroanthraquinone is in itself known; for example, its preparation is described in Ann. 501, page 247 and 286 (1933). 1,4,4a,9a-Tetrahydroanthraquinone can be employed, within the scope of the process according to the invention, either in the pure form or in the form of mixtures containing 1,4,4a,9a-tetrahydroanthraquinone. Examples of suitable mixtures containing 1,4,4a,9a-tetrahydroanthraquinone are those which contain naphthalene and/or phthalic anhydride and/or phthalic acid. For example, it is possible to employ mixtures which in addition to 1,4,4a,9a-tetrahydroanthraquinone contain 1 to 99% by weight of naphthalene and/or 1 to 99% by weight of phthalic anhydride. If phthalic acid is present in such mixtures, its amount is in general up to about 5% by weight, mixtures containing about 0.1 to 1.5% by weight of phthalic acid being preferred.

The use of 1,4,4a,9a-tetrahydroanthraquinone mixtures, such as are obtained on further processing the mixture of 1,4-naphthoquinone, phthalic anhydride and naphthalene, obtained on gas phase oxidation of naphthalene, by reacting this mixture with butadiene to give 1,4,4a,9a-tetrahydroanthraquinone, is preferred. This 1,4,4a,9a-tetrahydroanthraquinone mixture can also be further processed, completely or partially, to 9,10-anthraquinone. This further processing is in itself known and is described, for example, in DOS (German Published Specification) 2,245,555. The mixtures containing 1,4,4a,9a-tetrahydroanthraquinone, thereby obtained, in general have the following composition: about 1 to 25% by weight of 1,4,4a,9a-tetrahydroanthraquinone, about 1 to 90% by weight of naphthalene, about 1 to 90% by weight of phthalic anhydride and optionally about 0 to 5% by weight of phthalic acid. The use of mixtures composed of about 3 to 20% by weight of 1,4,4a,9a-tetrahydroanthraquinone, about 30 to 80% by weight of naphthalene, about 3 to 50% by weight of phthalic anhydride and about 0.3 to 1.0% by weight of phthalic acid is particularly preferred.

In general, the process according to the invention is carried out by taking liquid phthalic anhydride containing 1,4-naphthoquinone, adding the 1,4,4a,9a-tetrahydroanthraquinone, in the pure form or in the form of one of the mixtures described above, either as a solid or a liquid, heating the reaction mixture, whilst stirring, to temperatures from about 200° to 300° C., preferably about 240° to 260° C. and keepint it at this temperature for some time. In general, an advantageous reaction time has proved to be from 15 minutes to 10 hours, and from 0.5 to 4 hours in general suffices. The amount of 1,4,4a,9a-tetrahydroanthraquinone added is in general from about 0.3 to 3 mols per mol of 1,4-naphthoquinone. Preferably, an amount of about 0.8 to 1.5 mols per mol of 1,4-naphthoquinone is added. Pure phthalic anhydride (purity, for example, 99.7 to 99.95%) can be isolated from the reaction product of the heat treatment, in a manner which is in itself known, for example by distillation.

The process according to the invention can be carried out under normal pressure, reduced pressure or elevated pressure. Furthermore, it can be carried out continuously or discontinuously, and if it is carried out continuously, this may be done in a manner familiar to those skilled in the art, for example in a stirred kettle cascade or in a residence tube. A particular embodiment of the process according to the invention consists of carrying out the heat treatment of the crude phthalic anhydride, containing 1,4-naphthoquinone, with 1,4,4a,9a-tetrahydroanthraquinone or mixtures containing the latter in the virtually complete absence of molecular oxygen. This can be achieved, for example, by blanketing the reaction mixture with nitrogen or other inert gases.

The phthalic anhydride containing 1,4-naphthoquinone which is employed in the process according to the invention can have been obtained in any desired manner and can also contain further impurities, for example phthalic acid, anthraquinone, naphthalene and/or maleic anhydride. The use of the reaction products formed in the gas phase oxidation of naphthalene, such as are obtained, for example, in accordance with the processes described in U.S. Pat. Nos. 2,753,357, 2,765,323, 2,809,939 and 2,863,884, is preferred. The use of phthalic anhydride containing 1,4-naphthoquinone, as obtained by gas phase oxidation of naphthalene, and subsequent reaction of the product thereby obtainable with butadiene to 1,4,4a,9a-tetrahydroanthraquinone to anthraquinone (see, for example, DOS (German Published Specification) No. 2,245,555) is particularly preferred. In this case it is possible to use a part of the 1,4,4a,9a-tetrahydroanthraquinone hereby formed, in the pure form or as a mixture with naphthalene and/or phthalic anhydride, in order to purify the phthalic anhydride containing 1,4-naphthoquinone, and thus to avoid the addition of compounds which are foreign to the system; this facilitates further working up. In this way, anthraquinone and pure phthalic anhydride can be produced in one process.

The process according to the invention can be employed in a technically advantageous manner, in three different embodiments, within the framework of the anthraquinone process, starting from naphthalene, air and butadiene, the process being carried out continuously.

EMBODIMENT I

In this embodiment, the mixture containing 1,4,4a,9a-tetrahydroanthraquinone is added after completed oxydehydrogenation of the 1,4,4a,9a-tetrahydroanthraquinone contained in the main stream to anthraquinone, before the column for separating off the napthalene in the anthraquinone working-up part of the anthraquinone process, in which the heat treatment is carried out.

EMBODIMENT II

In this embodiment, the mixture containing 1,4,4a,9a-tetrahydroanthraquinone is added after completed oxydehydrogenation of the 1,4,4a,9a-tetrahydroanthraquinone, contained in the main stream, to anthraquinone, and after the naphthalene contained in the product stream has been separated off, before the column for separating off the phthalic anhydride in the anthraquinone working-up part of the anthraquinone process, in which the heat treament is carried out.

EMBODIMENT III

In this embodiment, the procedure followed is that the oxydehydrogenation of the 1,4,4a,9a-tetrahydroanthraquinone does not take place quantitatively in the part of the installation provided for the purpose, and the heat treatment is carried out in the column for separating off the naphthalene in the working-up part of the anthraquinone process.

The embodiments are explained in more detail with the aid of the Block Diagram 1.

The blocks A, B and C represent reaction stages in the anthraquinone process. The blocks E and D are components of the anthraquinone working-up part of the anthraquinone process.

Stream 1 from the oxidation of naphthalene, consisting of naphthalene, phthalic anhydride and naphthoquinone, is reacted, in apparatus A, with butadiene (stream 2). This gives stream 3, consisting of naphtalene, phthalic anhydride, butadiene, 1,4,4a,9a-tetrahydroanthraquinone and minor amounts of naphthoquinone and/or naphthohydroquinone. The butadiene is separated off in apparatus B (stream 4).

Stream 5, thus obtained, consisting of naphthalene, phthalic anhydride, 1,4,4a,9a-tetrahydroanthraquinone and minor amounts of naphthoquinone and/or naphthohydroquinone, is passed to apparatus C. Stream 6, consisting of phthalic anhydride and a gas containing molecular oxygen, is also passed to apparatus C. In apparatus C, the oxydehydrogenation of 1,4,4a,9a-tetrahydroanthraquinone to anthraquinone takes place. If the oxydehydrogenation takes place quantitatively, stream 7 contains naphthalene, phthalic anhydride, anthraquinone, small amounts of naphthoquinone and higher-boiling compounds. Stream 7 is passed to a column D, in which the naphthalene (stream 8) is separated off. This gives stream 9 which is composed of phthalic anhydride, anthraquinone, small amounts of naphthoquinone and higher-boiling compounds. In column E, stream 9 is separated into a stream 10, consisting of phthalic anhdyride, and a stream 11, consisting of anthraquinone and higher-boiling compounds.

In embodiment I, stream 5 is divided into a main stream which is passed to appartus C, and a part-stream which bypasses apparatus C and is fed into stream 7 before column D.

In embodiment II, the stream 5 is divided into a main stream which is passed to apparatus C and a part-stream which bypasses apparatus C and column D and is fed into stream 9 before column E.

In the third embodiment, the streams are not divided up. However, the reaction is carried out in apparatus C in such a way that the oxydehydrogenation of 1,4,4a,9a-tetrahydroanthraquinone to anthraquinone does not take place quantitatively. Stream 7 then still contains small amounts of 1,4,4a,9a-tetrahydroanthraquinone in addition to naphthalene, phthalic anhydride, anthraquinone, small amounts of naphthoquinone and/or naphthohydroquinone and higher-boiling compounds.

According to the three embodiments described above, it is not necessary to subject the phthalic anhydride, obtained as stream 10, to a chemical treatment to remove naphthoquinone.

If the procedure according to embodiments I, II or III is not followed, the removal of the naphthoquinone from the phthalic anhydride obtained as stream 10 can be carried out in a separate reaction stage. Distillation then gives naphthoquinone-free phthalic anhydride. The sump product thereby obtained can be recycled into streams 5 and/or 7 and/or 9.

The process according to the invention has the advantages that virtually no corrosion problems arise and that a continuous method of working is possible, without problems.

EXAMPLE 1

A mixture of 0.5 g of 1,4-naphthoquinone, 0.7 g of 1,4,4a,9a-tetrahydroanthraquinone and 98.8 of phthalic anhydride is kept in a glass flask, under a blanket of nitrogen, for 3 hours at 250° C. After the reaction product has cooled, the content of 1,4-naphthoquinone is determined by gas chromatography.

After the heat treatment, the content of 1,4-naphthoquinone is less than 5 ppm.

The same experiment, but without addition of 1,4,4a,9a-tetrahydroanthraquinone, gives, after cooling, a reaction product which contains 4,500 ppm of 1,4-naphthoquinone.

EXAMPLE 2

100 g of a crude phthalic anhydride which has been obtained in accordance with Ullmann, Encyclopädie der technischen Chemie (Encyclopaedia of Industrial Chemistry), 3rd edition, volume 13, page 720 to 721, by gas phase oxidation of naphthalene, and which contains 0.5% by weight of 1,4-naphthoquinone, is heated, after addition of 2 g of 1,4,4a,9a-tetrahydroanthraquinone, for 3 hours to 250° C. under a nitrogen blanket. After the reaction product has cooled, the content of 1,4-naphthoquinone is determined by gas chromatography. After the heat treatment, the content of naphthoquinone is less than 5 ppm.

EXAMPLE 3

5 kg/hour of crude phthalic anhydride (0.5% by weight of 1,4-naphthoquinone, 0.1% by weight of 9,10-anthraquinone, 1.0% by weight of phthalic acid, 10.0% by weight of naphthalene and 88.4% by weight of phthalic anhydride) are heated-treated continuously with 0.6 kg/hour of a 1,4,4a,9a-tetrahydroanthraquinone mixture (6.0% by weight of 1,4,4a,9a-tetrahydroanthraquinone, 6.0% by weight of phthalic anhydride, 0.5% by weight of 1,4-naphthoquinone and 87.5% by weight of naphthalene) at 250° C., under a nitrogen blanket, in a kettle cascade of 5 kettles each of 5 l capacity. The product leaving the kettle cascade is freed in a first distillation stage, in a manner which is in itself known, from the constituents which boil lower than phthalic anhydride, above all naphthalene. In a second distillation stage, about 4 kg/hour of pure phthalic anhydride containing less than 5 ppm of naphthoquinone are taken off at the top, whilst 0.4 kg/hour of sump products (10% by weight of 9,10-anthraquinone, 75% by weight of phthalic anhydride and 15% by weight of higher-boiling compounds) are fed to an anthraquinone working-up stage.

EXAMPLE 4

A mixture of 0.5 g of 1,4-naphthoquinone, 0.7 g of 1,4,4a,9a-tetrahydroanthraquinone and 98.8 g of phthalic anhydride is kept for 2 hours at 290° C. in a glass flask under a blanket of nitrogen. After the reaction product has cooled, the content of 1,4-naphthoquinone is determined by gas chromatography.

After the heat treatment, the content of 1,4-naphthoquinone is less than 5 ppm.

EXAMPLE 5 (see Diagram 1)

70 kg/hour of stream 7, consisting of 0.3% by weight of 1,4-naphthoquinone, 42.9% by weight of naphthalene, 42.9% by weight of phthalic anhydride, 10.0% by weight of anthraquinone and 2.9% by weight of unknown higher-boiling compounds are separated, by distillation, in apparatus D. Naphthalene is taken off virtually quantitatively at the top (stream 8). The sump product of apparatus D (stream 9) is separated in apparatus E. At the top of apparatus E, about 30 kg/hour of a product having the following composition are obtained: 0.7% by weight of 1,4-naphthoquinone, 99.0% by weight of phthalic anhydride and 0.3% by weight of unknown by-products.

EXAMPLE 6 (see Diagram 1)

A part-stream of 2.5 kg/hour of stream 5 is fed into stream 7 (see Example 5) (embodiment 1). Stream 5 has the following composition: 0.5% by weight of 1,4-naphthoquinone, 12.0% by weight of 1,4,4a,9a-tetrahydroanthraquinone, 13.0% by weight of phthalic anhydride, 74.0% by weight of naphthalene and 0.5% by weight of unknown by-products.

Working up takes place as in Example 5. At the top of apparatus E, about 30 kg/hour of a product having the following composition are obtained: <10 ppm of 1,4-naphthoquinone, 99.7% by weight of phthalic anhydride and 0.3% by weight of unknown by-products.

EXAMPLE 7 (see Diagram 1)

A part-stream of 2.5 kg/hour of stream 5 is fed into stream 9 (see Example 5) (embodiment 2). Stream 5 has the following composition: 0.5% by weight of 1,4-naphthoquinone, 12.0% by weight of 1,4,4a,9a-tetrahydroanthraquinone, 13.0% by weight of phthalic anhydride, 74.0% by weight of naphthalene and 0.5% by weight of unknown by-products.

Working up takes place as in Example 5. At the top of apparatus E about 30 kg/hour of a product having the following composition are obtained: <10 ppm of 1,4-naphthoquinone, 99.7% by weight of phthalic anhydride and 0.3% by weight of unknown by-products.

EXAMPLE 8 (see Diagram 1)

The oxidation of 1,4,4a,9a-tetrahydroanthraquinone to give 9,10-anthraquinone is controlled so that an equimolar amount of 1,4,4a,9a-tetrahydroanthraquinone, relative to 1,4-naphthoquinone, is still present in stream 7. 70 kg/hour of stream 7, consist of 0.3% by weight of 1,4-naphthoquinone and 1,4-naphthohydroquinone, 0.5% by weight of 1,4,4a,9a-tetrahydroanthraquinone, 42.9% by weight of naphthalene, 42.9% by weight of phthalic anhydride, 9.5% by weight of 9,10-anthraquinone and 2.9% by weight of unknown higher-boiling compounds are worked up as in Example 5. At the top of apparatus E, about 30 kg/hour of a product having the following composition are obtained: <10 ppm of 1,4-naphthoquinone, 99.7% by weight of phthalic anhydride and 0.3% by weight of unknown by-products.

What is claimed is:

1. Process for removing 1,4-naphthoquinone from phthalic anhydride which comprises subjecting phthalic anhydride-containing 1,4-naphthoquinone, or mixtures containing phthalic anhydride and also containing 1,4-naphthoquinone, to a heat treatment at temperatures from about 200° to 300° C. in the presence of 1,4,4a,9a-tetrahydroanthraquinone.

2. Process according to claim 1, characterized in that about 0.3 to 3 mols of 1,4,4a,9a-tetrahydroanthraquinone are employed per mol of 1,4-naphthoquinone.

3. Process according to claim 2, characterized in that about 0.8 to 1.5 mols of 1,4,4a,9a-tetrahydroanthraquonone are employed per mol of 1,4-naphthoquinone.

4. Process according to claim 1, characterized in that a mixture containing 1,4,4a,9a-tetrahydroanthraquinone is employed, which contains naphthalene and phthalic anhydride as the essential constituents.

5. Process according to claim 1, characterized in that the heat treatment is carried out at temperatures of about 240° to 260° C.

6. Process according to claim 1, characterized in that the heat treatment of the phthalic anhydride, containing 1,4-naphthoquinone, with 1,4,4a,9a-tetrahydroanthraquonine is carried out in the virtually complete absence of molecular oxygen.

7. Process according to claim 1, characterized in that pure phthalic anhydride is isolated by distillation from the reaction product after the heat treatment.

8. Process according to claim 1, characterized in that the heat treatment lasts 15 minutes to 10 hours.

9. Process according to claim 1, characterized in that the heat treatment is carried out in a stirred kettle cascade.

10. Process according to claim 1, characterized in that phthalic anhydride, containing 1,4-naphthoquinone, which has been obtained by gas phase oxidation of naphthalene is employed.

11. Process according to claim 1, characterized in that phthalic anhydride, containing 1,4-naphthoquinone, which has been obtained by gas phase oxidation of naphthalene, subsequent reaction of the product thereby obtainable with butadiene to give 1,4,4a9a-tetrahydroanthraquinone and reaction of the 1,4,4a,9a-tetrahydroanthraquinone to anthraquinone is employed.

12. Process according to claim 1, characterized in that the heat treatment is carried out in a column for separating off the naphthalene in the antraquinone working-up part of the anthraquinone process.

13. Process according to claim 1, characterized in that the heat treatment is carried out in the column for isolating the phthalic anhydride in the anthraquinone working-up part of the anthraquinone process.

14. Process according to claim 1, characterized in that the heat treatment is carried out in the column for isolating the naphthalene in the anthraquinone working-up part of the anthraquinone process, the 1,4,4a,9a-tetrahydroanthraquinone required for removing 1,4-naphthoquinone being available as a result of incomplete oxidation of the 1,4,4a,9a-tetrahydroanthraquinone to 9,10-anthraquinone in the column.

* * * * *